United States Patent [19]

Geary

[11] Patent Number: 4,675,177

[45] Date of Patent: Jun. 23, 1987

[54] ANTIPERSPIRANT COMPOSITIONS

[75] Inventor: Daniel C. Geary, Randolph, N.J.

[73] Assignee: American Cyanamid Company, Stamford, Conn.

[21] Appl. No.: 421,946

[22] Filed: Sep. 23, 1982

Related U.S. Application Data

[63] Continuation of Ser. No. 195,563, Oct. 9, 1980, abandoned, which is a continuation of Ser. No. 42,652, May 25, 1979, abandoned.

[51] Int. Cl.$^4$ .......................... A61K 7/32; A61K 7/34; A61K 7/38
[52] U.S. Cl. ........................................ 424/47; 424/66; 424/68
[58] Field of Search .................................... 424/47, 68

[56] References Cited

U.S. PATENT DOCUMENTS

| | | | |
|---|---|---|---|
| 2,373,198 | 4/1945 | Roehrich | 424/68 X |
| 2,571,030 | 10/1951 | Govett et al. | 424/68 X |
| 2,876,163 | 3/1959 | Garizio et al. | 424/68 |
| 3,030,274 | 4/1962 | Grant | 424/68 X |
| 4,005,189 | 1/1977 | Reese et al. | 424/47 |
| 4,025,615 | 5/1977 | Rubino | 424/68 |

Primary Examiner—Dale R. Ore
Attorney, Agent, or Firm—Charles J. Fickey

[57] ABSTRACT

Antiperspirant compositions having aluminum or aluminum-zirconium salts as the active ingredients and containing particular lactate, citrate, tartrate or adipate esters to provide enhanced antiperspirant efficacy. The compositions may be formulated in the form of sticks, liquid roll-on and pump or aerosol sprays.

17 Claims, No Drawings

ANTIPERSPIRANT COMPOSITIONS

This is a continuation of application Ser. No. 195,563, filed Oct. 9, 1980, now abandoned, which is a continuation of Ser. No. 42,652, filed May 25, 1979, now abandoned.

FIELD OF THE INVENTION

The invention relates to improved antiperspirant compositions containing aluminum or aluminum-zirconium salts as the active material and, in particular, to antiperspirant stick, liquid roll-on, pump spray and aerosol spray compositions containing certain lactate, citrate, tartrate or adipate esters to provide enhanced antiperspirant efficacy.

BACKGROUND OF THE INVENTION

Antiperspirant compositions generally contain an aluminum or aluminum-zirconium astringent salt as active astringents. The also contain fatty alcohols, waxes, fatty amides and emollients which may include liquid fatty acid esters, silicones, mineral oil, propoxylated alcohols, etc. All of these materials tend to coat the particle of the astringent material when the product is applied to the axilla preventing subsequent water or perspiration from permeating thru the coating to the astringent salt to activate the astringent. This results in delayed onset of activity. Moreover, in the case of aerosol sprays, they are generally comprised of low levels (5-10%) of active ingredient, e.g., aluminum chlorohydrate, dispersed in a nonvolatile, nonhygroscopic liquid vehicle, such as the above mentioned fatty esters, propoxylated materials, silicones, and the like. Typical formulations containing about 5% aluminum chlorohydrate provide about 15-35% sweat reduction and very low speed of onset of activity. An antiperspirant composition is needed which has faster onset, high efficacy, nonstaining, nontacky, and in the case of sprays, nonclogging characteristics, along with good residual feel and a perception of fast drying.

SCOPE OF THE INVENTION

The present invention provides antiperspirant compositions which exhibit improved antiperspirant efficacy by the incorporation into the composition of a certain lactate, citrate, tartrate, or adipate esters, thus improving permeability of moisture through the normally difficulty permeable coating surrounding the astringent metal salt particles. Thus up to 25 weight percent of the astringent metal salt may be incorporated in the composition.

ADVANTAGES OF THE INVENTION

The incorporation of the esters of the invention into an antiperspirant stick composition provides faster onset of maximum antiperspirant activity and higher maximum efficacy at the 22-hour check point in clinical testing, probably because the esters have a high dielectric constant, permitting moisture to permeate the film surrounding the active astringent material. Some esters are water soluble, which permits the use of aqueous solutions of aluminum salts rather than dry salts. This provides faster onset of antiperspirant activity and yet provides a dry feeling antiperspirant. The esters provide nonstaining sticks, an excellent residual feel (cool, nonoily, nontacky) and provide nonwhitening sticks which are appealing to women.

The aerosols of the present invention can contain up to 25% by weight of astringent aluminum salt, e.g., aluminum chlorohydrate, thereby greatly increasing efficacy, while at the same time reducing the tendency of valve clogging. The esters of the invention have the ability to hold water regardless of relative humidity and would prevent "drying out" of the solid salt or 50% aqueous solution in the valve actuator and valve stem particularly at high astringent levels (clogging is not a problem at low (5%) aluminum chlorohydrate content). The esters also reduce clogging in pump sprays.

The esters are not volatile and remain on the astringent particle. However, because of their high dielectric constant, water of perspiration readily permeates the coating to activate the astringent. This leads to fast onset of activity and increases efficacy. Without the use of the invention esters raising the level of salt to 25% with conventional emollients will not provide faster onset of a higher efficacy at the 22-hour checkpoint in clinical testing. These esters provide nonstaining compositions whereas conventional antiperspirants contain emollients such as isopropyl myristate, which hydrolyzes in the axilla to isopropanol and myristic acid. The esters of the invention hydrolyze to propylene glycol, butylene glycol, glycerol, and lactic, citric, or tartaric acid. Myristic acid reacts with the aluminum salt to form aluminum myristate, a grease which is difficult to remove from clogging. On the other hand, lactic acid, for example, reacts to form aluminum lactate which is water soluble, along with the glycols, and is easily removed by washing.

The esters also provide a velvety feel and are less discernible than conventional emollients which have an oily, tacky feel.

DESCRIPTION OF THE INVENTION

The compositions of the present invention contain from about 3 to 25 weight percent of an astringent metal salt and from about 0.5 to 70 weight percent of a lactate, citrate, tartrate or adipate ester of an alkylene diol or triol, or pentaerythrytol for example. Other materials are incorporated to form a stick, liquid, roll-on, liquid pump or aerosol spray as required. Suitable active astringents include aluminum sulfate, aluminum chloride, aluminum chlorohydroxide, aluminum sulfocarbolate, zinc sulfate, zirconium salts, such as zirconium chlorohydroxide, combinations of aluminum chloride and aluminum-zirconium hydroxychloride, and the like. Aluminum chlorohydroxide and aluminum-zirconium chlorohydroxide are preferred. They may be used as solutions (aqueous) or as the granular or impalpable form.

Suitable ester compounds are as follows, with their preferred antiperspirant composition form:

For use in antiperspirant sticks:
1,3 butanediol mono and dilactates
trimethylol propane trilactate
hexyl and ethyl hexyl lactate
1,6 hexanediol lactate
1,2,6 hexanetriol lactate
ethyl hexanediol lactate
ethyl hexanetriol lactate
hexyl and ethyl hexyl tartrate
1,6 hexanediol tartrate
1,2,6 hexanetriol tartrate
ethyl hexanediol tartrate
ethyl hexanetriol tartrate
di-1,6 hexanediol tartrate diethyl hexyldiol tartrate
dihexyl tartrate
diethyl hexyl tartrate
hexyl and ethyl hexyl citrate
1,6 hexanediol citrate 1,2,6 hexanetriol citrate
ethyl hexanediol citrate
ethyl hexanetriol citrate
di-1,6 hexanediol citrate
diethyl hexanediol citrate
dihexyl citrate
diethyl hexyl citrate
1,3 butanediol mono and diadipates
diisopropyl adipate
hexyl and ethyl hexyl adipate
dihexyl and diethyl hexyl adipate
1,6 hexanediol adipate
1,2,6 hexanetriol adipate
ethyl hexanediol adipate
ethyl hexanetriol adipate
di-1,6 hexanediol adipate
diethyl hexanediol adipate
mono and di ethylene glycol lactates, citrates, tartrates and adipates For use with roll-on or pump sprays:

propylene glycol mono and dilactate, tartrate, citrate and adipate
1,3 butanediol mono and dilactate, tartrate, citrate and adipate
glycerol mono, di and trilactate, tartrate, citrate and adipate
trimethylol propane lactate, tartrate, citrate and adipate
pentaerythyritol lactate, tartrate, citrate and adipate
dipropylene glycol tartrate, citrate and adipate
diglycerol tartrate, citrate and adipate
ditrimethylol propane tartrate, citrate and adipate
dipentaerythritol tartrate, citrate and adipate For use with aerosol sprays: All esters for antiperspirant sticks and the following additional esters:

Propylene glycol mono and dilactates, citrates, tartrates and adipates
1,3 butanediol mono and dicitrate, tartrate and adipates
glycerol mono, di and trilactate, citrate, tartrate and adipates

PREPARATION OF A STICK FORMULATION

The esters are useful in a stick antiperspirant composition in combination with the ethoxylated fatty alcohols, represented by the formula:

$$RO-(CH_2CH_2O)_{\overline{n}}H$$

wherein R represents the aliphatic portion of a fatty alcohol of 12 to 20 carbon atoms, preferably 16 to 18 carbon atoms, and n is an integer from about 100 to 200. Polyethoxylated steryl alcohol and cetyl alcohol are preferred.

The antiperspirant stick compositions also may contain a fatty alcohol base, such as stearyl alcohol or cetyl alcohol, or mixtures thereof, or a fatty acid amide or other synthetic and natural polymers which do not dissolve in or disperse completely or quickly in water.

In general, the antiperspirant stick compositions will comprise a waxy base, which may be a combination of an ethoxylated fatty alcohol and a fatty alcohol, fatty acid amide, or the like, or an ethoxylated fatty alcohol or fatty alcohol or fatty acid amide alone. The antiperspirants will contain one or more active astringent ingredients and one or more of the esters of the invention.

Other ingredients, for example, alcohol, water, suspending agents such as Bentones, which are organically treated montmorillonite clays, silica, fragrances, and the like, may also be included.

The compositions of the invention contain from about 10 to 25 percent by weight of astringent metal salt compound, preferably about 15 to 25 percent, in a wax-like base comprising from about 6 to 35 percent by weight of the antiperspirant composition. From about 5 to 20 weight percent of said antiperspirant comprises a wax-like fatty alcohol and from about one to 15 weight percent of said antiperspirant comprises an ethoxylated fatty alcohol. The lactate, citrate, tartrate or adipate esters comprise from about 0.5 to 60 percent by weight of the composition.

Specific examples of stick formulations are set forth in the following Examples 1 to 6:

EXAMPLE 1

| Ethoxylated Stearyl alcohol (1) | 1.0 |
| --- | --- |
| Stearyl alcohol | 20.0 |
| Aluminum chlorohydroxide | 25.0 |
| Diethyl hexyl adipate | 52.8 |
| Fumed silica (2) | 0.4 |
| Fragrance | 0.6 |
| | 100.0 |

(1) $CH_3-(CH_2)_{17}O-(CH_2CH_2O)_{100}H$
(2) Silane treated, hydrophobic, TULLANOX 500 (Cabot, Inc.)

EXAMPLE 2

| Ethoxylated Cetyl alcohol (1) | 1.0 |
| --- | --- |
| Cetyl alcohol | 20.0 |
| Aluminum chlorohydroxide (3) | 25.0 |
| Ethyl alcohol | 20.0 |
| Water | 5.0 |
| 1,3-Butanediol monolactate | 22.4 |
| Fragrance | 0.6 |
| | 100.0 |

(3) Organically treated to be alcohol soluble

EXAMPLE 3

| Ethoxylated Stearyl alcohol (1) | 1.0 |
| --- | --- |
| Stearyl alcohol | 20.0 |
| Aluminum/zirconium chlorohydroxide | 29.0 |
| Fumed silica (2) | 0.2 |
| 1,3-Propylene glycol monolactate | 49.7 |
| Fragrance | 0.6 |
| | 100.0 |

EXAMPLE 4

| Ethoxylated Cetyl alcohol (4) | 1.0 |
| --- | --- |
| Cetyl alcohol | 17.0 |
| Aluminum chlorohydroxide | 15.0 |
| Aluminum chlorohydroxide (50% aqueous solution) | 20.0 |
| Fumed silica | 2.0 |
| 1,3-Propylene glycol monolactate | 44.4 |
| Fragrance | 0.6 |
| | 100.0 |

(4) $CH_3-(CH_2)_{14}CH_2O-(CH_2CH_2O)_{100}H$

EXAMPLE 5

| Ethoxylated Stearyl alcohol | 1.0 |
|---|---|
| Stearyl alcohol | 20.0 |
| Aluminum chlorohydroxide | 25.0 |
| Bentonite clay (5) | 0.5 |
| 1,3-Butanediol monolactate | 52.9 |
| Fragrance | 0.6 |
| | 100.0 |

(5) Organically treated Montmorillonite clay

EXAMPLE 6

| Ethoxylated Stearyl alcohol | 1.0 |
|---|---|
| Stearyl alcohol | 20.0 |
| Aluminum chloride hexahydrate (50% aqueous) | 4.0 |
| Fumed silica | 0.4 |
| 1,3-Propylene glycol monolactate | 73.8 |
| Fragrance | 0.6 |
| | 100.0 |

PREPARATION OF A ROLL-ON FORMULATION

The astringent metal salt is used in an amount of from about 15 to 25 weight percent with from about 0.5 to 70 weight percent of the ester of the invention.

The esters of the invention may be used in combination with small amounts (0.5–8 weight percent) of other, more conventional emollients, or functional additives which may be added for reasons other than antiperspirant efficacy, such as thickeners, viscosity stabilizers, fragrance solubilizers, opacifiers, etc.

The roll-on compositions may also contain ethoxylated fatty alcohols, such as ethoxylated stearyl alcohol or ethoxylated stearic acid, or ethoxylated cetyl or lauryl alcohol, or combinations thereof, containing 100 to 200 moles of combined ethylene oxide. Those containing high ethylene oxide content tend to be more permeable to moisture, thus further increasing antiperspirant onset and efficacy. The lower ethoxylated compounds, i.e., containing about 100 moles of ethylene oxide, are preferred. However, the highly ethoxylated materials are not essential to the inventive roll-on composition.

Specific examples of roll-on formulations are set forth in the following Examples 7 to 9.

EXAMPLE 7

A roll-on composition was prepared having the following ingredients:

| | Parts by Weight |
|---|---|
| Glyceryl monostearate | 2.15 |
| 100 POE stearic acid | 3.23 |
| Magnesium aluminum silicate; acid stable | 1.00 |
| Aluminum chlorohydrate (50% aqueous solution) | 50.00 |
| 1,3-Propylene glycol monolactate | 9.30 |
| Fragrance | 0.30 |
| Dye Color | 0.02 |
| Water | 34.00 |
| | 100.00 |

*100 POE stearate is stearic acid ethoxylated with 100 moles of ethylene oxide.

EXAMPLE 8

Roll-on antiperspirant formulations are prepared as follows:

| | Parts by Weight | |
|---|---|---|
| | A | B |
| Glyceryl monostearate | 5.00 | 3.50 |
| Magnesium aluminum silicate | 0.50 | 1.00 |
| 100 POE stearyl alcohol | 5.00 | 3.50 |
| Aluminum chlorohydrate (50%) | 30.00 | 48.00 |
| 4 POE lauryl alcohol* | 1.50 | 0.50 |
| 23 POE stearyl alcohol** | 4.50 | 1.50 |
| Fragrance | 1.00 | 0.00 |
| 1,3-Propylene glycol monolactate | 8.00 | — |
| 1,3-Butylene glycol monolactate | — | 10.00 |
| Water | 44.50 | 32.00 |
| | 100.00 | 100.00 |

*lauryl alcohol condensed with an average of 4 moles of ethylene oxide
**stearyl alcohol condensed with an average of 23 moles of ethylene oxide

EXAMPLE 9

| | Parts by Weight |
|---|---|
| PPG stearyl ether (2) | 4.70 |
| POE-2-stearyl ether | 1.00 |
| Aluminum chlorohydrate (50%) | 50.00 |
| POE-100 stearyl ether | 1.00 |
| Fragrance | 0.30 |
| 1,3-Propylene glycol monolactate | 20.00 |
| Water | 23.00 |
| | 100.00 |

PREPARATION OF A PUMP SPRAY FORMULATION

The pump spray formulations may be prepared using solid aluminum chlorohydrate, aqueous solutions of aluminum chlorohydrate, or combinations of both. In general, pump spray formulations of the first type (solid aluminum chlorohydrate) will have the following composition:

| | Percent by Weight |
|---|---|
| Aluminum Chlorohydrate | 3.3–2.5 |
| Fumed silica or Bentone clay | 0.3–2.5 |
| Esters of the invention | 72.5–96.4 |
| Fragrance | as needed |

Formulations of the second type (aqueous aluminum chlorohdyrate) will have the following composition:

| | Percent by Weight |
|---|---|
| Aluminum chlorohydrate (50%) | 30–50 |
| Esters of the invention | 50–70 |
| Fragrance | as needed |

Formulations of the third type will have compositions as follows:

| | Percent by Weight |
|---|---|
| Aluminum chlorohydrate | 3.3–5.0 |
| Aluminum chlorohydrate (50%) | 30.0–50.0 |
| Hydrophobic fumed silica | 3.0–0.5 |
| Esters of the invention | 39.5–63.4 |

| | Percent by Weight |
|---|---|
| Fragrance | as needed |

The esters of the invention are used in an amount from about 40 to 96 percent by weight.

Other ingredients, such as talc or other solids, can be added to reduce cost and to impart a powdery feel. Liquids that function as fragrance solubilizers or impart feel, or pump lubricants may be used at levels at 0.1 to 9% in place of part of the ester used. In each formulation hydrocarbons, such as pentane or Shell Sol 71, could be added in place of a portion of the emollient if a container was used to which the hydrocarbon was impervious, and if a pump was used that could be primed without being in contact with the atmosphere at all times.

In addition to the above, other active astringents such as aluminum chloride (up to 15%) or equal amounts of aluminum-zirconium hydroxychloride, or other basic aluminum salts, may be added in place of all or part of the aluminum chlorohydrate.

Ethanol up to levels at 30% may be used in type two formuations for cost reduction and faster drying characteristics.

The following specific examples 10 to 12 illustrate pump spray formulations of the invention.

EXAMPLE 10

| | A | B | C |
|---|---|---|---|
| Aluminum chlorohydrate | 15.0 | 20.0 | 25.0 |
| Bentone 38 | — | 1.0 | 0.5 |
| Cab-O-Sil M-5 | 2.5 | — | — |
| 1,3-Propylene glycol monoactate | 82.5 | — | 74.0 |
| 1,3-Butylene glycol monoactate | — | 88.5 | — |
| Fragrance | — | 0.5 | 0.5 |

The formulations A–C are illustrative of those containing solid aluminum chlorohydrate.

EXAMPLE 11

| | D | E | F |
|---|---|---|---|
| Aluminum chlorohydrate (50%) | 30.0 | 40.0 | 50.0 |
| 1,3-Propylene glycol monolactate | 69.5 | 59.5 | — |
| 1,3-Butylene glycol monolactate | — | — | 49.5 |
| Fragrance | 0.5 | 0.5 | 0.5 |

Formulations D–F illustrate pump spray compositions utilizing aqueous solutions of aluminum chlorohydrate.

EXAMPLE 12

| | G | H | I |
|---|---|---|---|
| Aluminum chlorohydrate | 3.0 | 4.0 | 5.0 |
| Aluminum chlorohydrate (50% solution) | 50.0 | 40.0 | 30.0 |
| Hydrophobic fumed silica (Tullanox 500) | 5.0 | 3.0 | 5.0 |
| Fumed silica (Cab-O-Sil M-5) | 0.5 | 0.5 | 0.5 |
| 1,3-Propylene glycol monolactate | 41.0 | 52.0 | — |
| 1,3-Butylene glycol monoactate | — | — | 59.0 |
| Fragrance | 0.5 | 0.5 | 0.5 |

Formulations G–I illustrate the use of both dry and aqueous solutions of aluminum chlorohydrate.

PREPARATION OF AN AEROSOL FORMULATION

The astringent metal salt is added in an amount of about 3 to 25 percent by weight, preferably about 15 to 25 percent by weight. Aerosol compositions may be prepared using dry astringent salts, aqueous solutions of astringent, or mixtures of both. The preferred astringent is aluminum chlorohydrate. Aluminum chloride or other basic aluminum salts may also be used to replace part of the aluminum chlorohydrate.

The esters of the invention are used in an amount from about 3 to 60 weight percent.

Other ingredients may be added to improve feel or to lubricate the valve or as fragrance solubilizers. Bentones, fumed silica and Tullanox are added as suspending agents for the solid aluminum chlorohydrate. It is necessary to add Tullanox which is capable of holding 9 times its weight while remaining dry to the touch in order to incorporate 50% aqueous solutions of aluminum chlorohydrate.

The aerosol compositions contain a hydrocarbon propellant (propane, butane, pentane, isobutane, and mixtures thereof) in an amount of about 10 to 30 percent by weight of the total composition.

Aerosol formulations containing only dry aluminum chlorohydrate will generally have the following composition:

| | Weight Percent |
|---|---|
| Aluminum chlorohydrate | 3.0–25.0 |
| Bentone 38 or Cab-O-Sil M-5 | 0.3–2.5 |
| Fragrance | q.s. |
| Ester of the invention | 54.7–10.5 |
| Hydrocarbon propellant | 42.0–62.0 |

Aerosol formulations containing aqueous solution of aluminum chlorohydrate will generally have the following composition:

| | Weight Percent |
|---|---|
| Aluminum chlorohydrate (50%) | 30.0–50.0 |
| Hydrophobic fumed silica | 3.0–5.0 |
| Ester of the invention | 25.0–21.0 |
| Hydrocarbon propellant | 42.0–24.0 |
| Fragrance | q.s. |

Aerosol formulations in which both dry aluminum chlorohydrate and aqueous solution thereof are used will generally conform to the composition:

| | Weight Percent |
|---|---|
| Aluminum chlorohydrate | 3.3–5.0 |
| Aluminum chlorohydrate (50%) | 50.0–30.0 |
| Fumed silica | 0.3–0.5 |
| Hydrophobic fumed silica | 5.0–3.0 |
| Ester of the invention | 21.4–19.5 |
| Hydrocarbon propellant | 20.0–42.0 |

|  | Weight Percent |
|---|---|
| Fragrance | q.s. |

The following specific examples 13 to 15 illustrate aerosol formulations of the invention:

EXAMPLE 13

|  | A | B | C |
|---|---|---|---|
| Aluminum chlorohydrate | 3.0 | 15.0 | 25.0 |
| Bentone 38 | 0.3 | 1.5 | — |
| Cab-O-Sil M-5 | — | — | 2.5 |
| 1.3-Propylene glycol monolactate | 54.7 | — | 10.5 |
| 1,3-Butylene glycol monolactate | — | 31.5 | — |
| Hydrocarbon propellant | 42.0 | 52.0 | 62.0 |
| Fragrance | — | q.s. | q.s. |

EXAMPLE 14

|  | D | E | F |
|---|---|---|---|
| Aluminum chlorohydrate (50%) | 30.0 | 40.0 | 50.0 |
| Hydrophobic fumed silica | 3.0 | 4.0 | 5.0 |
| 1,3-Propylene glycol monolactate | 25.0 | — | 21.0 |
| 1,3-Butylene glycol monolactate | — | 24.0 | — |
| Hydrocarbon propellant | 42.0 | 32.0 | 24.0 |
| Fragrance | q.s. | q.s. | q.s. |

EXAMPLE 15

|  | G | H | I |
|---|---|---|---|
| Aluminum chlorohydrate | 3.3 | 4.0 | 5.0 |
| Aluminum chlorohydrate (50%) | 50.0 | 40.0 | 30.0 |
| Fumed silica | 0.3 | 0.4 | 0.5 |
| Hydrophobic fumed silica | 5.0 | 4.0 | 3.0 |
| 1,3-Propylene glycol monolactate | 21.4 | 20.0 | — |
| 1,3-Butylene glycol monolactate | — | — | 19.5 |
| Hydrocarbon propellant | 20.0 | 31.0 | 42.0 |
| Fragrance | q.s. | q.s. | q.s. |

I claim:

1. An antiperspirant composition comprising an astringent metal salt material and a lactate, citrate, tartrate or adipate ester wherein said ester moiety is a mono or polyhydric lower alkanol.

2. An antiperspirant stick composition comprising a wax-like fatty alcohol; an astringent metal salt material; and a lactate, citrate, tartrate or adipate ester as in claim 1.

3. A composition as in claim 2 comprising in addition an ethoxylated fatty alcohol represented by the formula:

$$RO-(CH_2CH_2O)_{\overline{n}}H$$

wherein R is an alkyl radical of about 16 to 18 carbon atoms and n is an integer of from about 100 to 200.

4. The composition of claim 1 wherein said astringent material is aluminum salt.

5. The composition of claim 4 wherein said salt is aluminum chlorhydrate.

6. The composition of claim 1 wherein said astringent material is an aluminum-zirconium salt.

7. The antiperspirant of claim 1 wherein said ester is 1,3 propylene glycol monolactate.

8. The antiperspirant of claim 1 wherein said ester is 1,3 butylene glycol monolactate.

9. The antiperspirant of claim 1 wherein said ester is 1,3 propylene glycol dilactate.

10. The antiperspirant of claim 1 wherein said ester is 1,3 butylene glycol dilactate.

11. The antiperspirant of claim 1 wherein said ester is glycerol monolactate.

12. The antiperspirant of claim 1 wherein said ester is glycerol dilactate.

13. The antiperspirant of claim 1 wherein said ester is glycerol trilactate.

14. The antiperspirant of claim 1 wherein said ester is trimethylolpropane lactate.

15. The antiperspirant of claim 1 wherein said ester is dihexyl adipate.

16. The antiperspirant of claim 1 wherein said ester is diethyl hexyl adipate.

17. A dry suspension antiperspirant comprising a pressure tight container, having a valve controlled opening and a valve for dispensing a liquid in aerosol form, said container containing an astringent metal salt dispersed in a liquid vehicle, and a liquid propellant which is gaseous at room temperature; said liquid vehicle being selected from a lactate, citrate, tartrate or adipate ester or mixtures thereof.

* * * * *